US011680934B2

(12) United States Patent
Weiss-Penzias et al.

(10) Patent No.: US 11,680,934 B2
(45) Date of Patent: Jun. 20, 2023

(54) SYSTEM AND METHOD FOR SENSING VOLATILE ORGANIC COMPOUNDS

(71) Applicant: The Regents of the University of California, Oakland, CA (US)

(72) Inventors: Peter Weiss-Penzias, Santa Cruz, CA (US); Mauricio Rojas-Andrade, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 434 days.

(21) Appl. No.: 16/894,042

(22) Filed: Jun. 5, 2020

(65) Prior Publication Data

US 2020/0386731 A1    Dec. 10, 2020

Related U.S. Application Data

(60) Provisional application No. 62/858,449, filed on Jun. 7, 2019.

(51) Int. Cl.
| | | |
|---|---|---|
| *G01N 33/00* | (2006.01) | |
| *G01N 27/40* | (2006.01) | |
| *C12M 1/04* | (2006.01) | |
| *C12G 1/00* | (2019.01) | |
| *B01D 47/00* | (2006.01) | |

(Continued)

(52) U.S. Cl.
CPC ........... *G01N 33/0047* (2013.01); *C12M 1/04* (2013.01); *C12M 47/18* (2013.01); *G01N 27/4078* (2013.01); *G01N 33/0073* (2013.01); *B01D 47/00* (2013.01); *B01D 2257/708* (2013.01); *C12G 1/00* (2013.01)

(58) Field of Classification Search
CPC ........... G01N 33/0047; G01N 27/4078; G01N 33/0073; G01N 27/127; C12M 1/04; C12M 47/18; B01D 47/00; B01D 2257/708; C12G 1/00
USPC ................. 204/424, 425, 426, 427, 428, 429
See application file for complete search history.

(56) References Cited

U.S. PATENT DOCUMENTS

| 6,068,686 | A | * | 5/2000 | Sorensen ............... B01D 50/60 |
| | | | | 96/138 |
| 2016/0199769 | A1 | * | 7/2016 | Worrilow ............... B01D 53/02 |
| | | | | 423/245.1 |

(Continued)

FOREIGN PATENT DOCUMENTS

| JP | 2010-042353 A | * | 2/2010 |
| RU | 2717698 C1 | * | 3/2020 |
| WO | WO 2012/044759 A2 | * | 4/2012 |

OTHER PUBLICATIONS

Machine-generated English translation of RU 2717698, generated on Sep. 15, 2022.*

(Continued)

*Primary Examiner* — Fred Prince
(74) *Attorney, Agent, or Firm* — Carter, DeLuca & Farrell LLP

(57) ABSTRACT

A gas sensor assembly includes a housing; an inlet assembly configured to carry a gaseous composition having a volatile organic compound into the housing; and an outlet assembly configured to carry the gaseous composition from the housing. The gas sensor assembly also includes an ultraviolet light source disposed within the housing and a gas sensor disposed within the housing and configured to sense an amount of the volatile organic compound.

18 Claims, 11 Drawing Sheets

(51) Int. Cl.
   *G01N 27/407*   (2006.01)
   *C12M 1/00*   (2006.01)

(56) References Cited

U.S. PATENT DOCUMENTS

2017/0082305 A1* 3/2017 Law .................. B01D 46/58
2019/0376940 A1* 12/2019 Debnath ............. G01N 33/004

OTHER PUBLICATIONS

Machine-generated English translation of JP 2010-042353, generated on Sep. 15, 2022.*

* cited by examiner

SYSTEM AND METHOD FOR SENSING VOLATILE ORGANIC COMPOUNDS

CROSS-REFERENCE TO RELATED APPLICATION

The present application claims the benefit of and priority to U.S. Provisional Application No. 62/858,449, filed on Jun. 7, 2019. The entire disclosure of the foregoing application is incorporated by reference herein.

BACKGROUND

Various ethanol producers, such as those in the wine and spirit industries, emit ethanol gas during fermentation. Current emissions from this sector are estimated based on liquid volumes lost during storage and no gas phase measurements are currently being made. Instrumentation that would traditionally be used to accurately quantify emissions is specialized and costly. Accordingly, there is a need for a sensing system configured to measure ethanol and other volatile organic compounds ("VOCs") that provides a low-cost alternative to conventional sensors.

SUMMARY

The present disclosure provides a system and method based on a low-cost and rugged gas sensor, which relies on semiconductive properties of metal oxide nanostructures. The sensor's conductance is proportional to the concentration of VOCs, such as ethanol. The sensor is used with an ultraviolet light source which stimulates and cleans an active surface of the sensor. The sensor may be operated at ambient temperature and is not adversely affected by moisture. The sensor is sensitive to the compounds of interest at concentrations relevant for the industries that need quantification of VOCs. In particular, the sensor is configured to quantify air emissions of ethanol and other VOCs and may be used in various industries such as wineries, breweries, industrial composting facilities, and the like.

According to one embodiment of the present disclosure, a gas sensor assembly is disclosed. The gas sensor assembly includes a housing; an inlet assembly configured to carry a gaseous composition having a volatile organic compound into the housing; and an outlet assembly configured to carry the gaseous composition from the housing. The gas sensor assembly also includes an ultraviolet light source disposed within the housing and a gas sensor disposed within the housing and configured to sense an amount of the volatile organic compound.

According to one aspect of the above embodiment, the gas sensor includes: a substrate; a conductive coating disposed on a surface of the substrate having a channel defined therein; and a metal oxide nanostructure layer disposed within the channel, the metal oxide nanostructure layer having a resistance, which varies in response to contact with the volatile organic compound. The metal oxide nanostructure layer includes zinc oxide nanostructures.

According to another aspect of the above embodiment, the conductive coating may include a first electrode pattern having a first plurality of finger electrodes and a second electrode pattern having a second plurality of finger electrodes. The first plurality of finger electrodes and the second plurality of finger electrodes define a channel having a tortuous pattern.

According to a further aspect of the above embodiment, the gas sensor assembly further includes an ohm meter coupled to the gas sensor, the ohm meter is configured to measure the resistance of the metal oxide nanostructure layer. The gas sensor assembly further includes a computing device coupled to the ohm meter, the computing device configured to determine the amount of the volatile organic compound.

According to one aspect of the above embodiment, the inlet assembly includes an intake flow control device and the outlet assembly includes an outlet flow control device. The computing device is configured to activate the intake flow control device to pump the gaseous composition into the housing until a pressure setpoint is reached. The computing device is further configured to activate the ultraviolet light source and determine the amount of the volatile organic compound after the pressure setpoint is reached. The computing device is further configured to actuate the outlet assembly to remove the gaseous composition out of the housing after determining the amount of the volatile organic compound According to another embodiment of the present disclosure, an exhaust system is disclosed. The exhaust system includes an upstream conduit configured to carry a gaseous composition having a volatile organic compound; a scrubber coupled to the upstream conduit and configured to remove at least a portion of the volatile organic compound; and a downstream conduit coupled to the scrubber and configured to carry the gaseous composition from the scrubber. The exhaust system also includes a first gas sensor assembly coupled to the upstream conduit and configured to measure a first concentration of the volatile organic compound upstream of the scrubber; a second gas sensor assembly coupled to the downstream conduit and configured to measure a second concentration of the volatile organic compound downstream of the scrubber; and a computing device coupled to the first gas sensor assembly and the second gas sensor assembly, the computing device configured to calculate a difference between the first concentration and the second concentration to determine efficiency of the scrubber.

According to one aspect of the above embodiment, each of the first gas sensor assembly and the second gas sensor assembly includes: a housing; an inlet assembly configured to carry a gaseous composition having a volatile organic compound into the housing; an outlet assembly configured to carry the gaseous composition from the housing; an ultraviolet light source disposed within the housing; and a gas sensor disposed within the housing and configured to sense an amount of the volatile organic compound.

According to another aspect of the above embodiment, the gas sensor includes: a substrate; a conductive coating disposed on a surface of the substrate having a channel defined therein; and a metal oxide nanostructure layer disposed within the channel, the metal oxide nanostructure layer having a resistance, which varies in response to contact with the volatile organic compound. The metal oxide nanostructure layer may include zinc oxide nanostructures.

According to a further aspect of the above embodiment, each of the first gas sensor assembly and the second gas sensor assembly further includes: an ohm meter coupled to the gas sensor, the ohm meter configured to measure the resistance of the metal oxide nanostructure layer.

According to another aspect of the above embodiment, the computing device is coupled to the ohm meter, the computing device is configured to determine the amount of the volatile organic compound.

According to yet another aspect of the above embodiment, the inlet assembly includes an intake flow control device and the outlet assembly includes an outlet flow control device. The computing device is further configured to activate the intake flow control device to pump the gaseous composition into the housing until a pressure setpoint is reached. The computing device is also configured to: activate the ultraviolet light source and determine the amount of the volatile organic compound after the pressure setpoint is reached; and activate the outlet flow control device to pump the gaseous composition out of the housing after determining the amount of the volatile organic compound.

BRIEF DESCRIPTION OF DRAWINGS

Various embodiments of the present disclosure will be described herein below with reference to the figures wherein.

DETAILED DESCRIPTION

Figure 1:
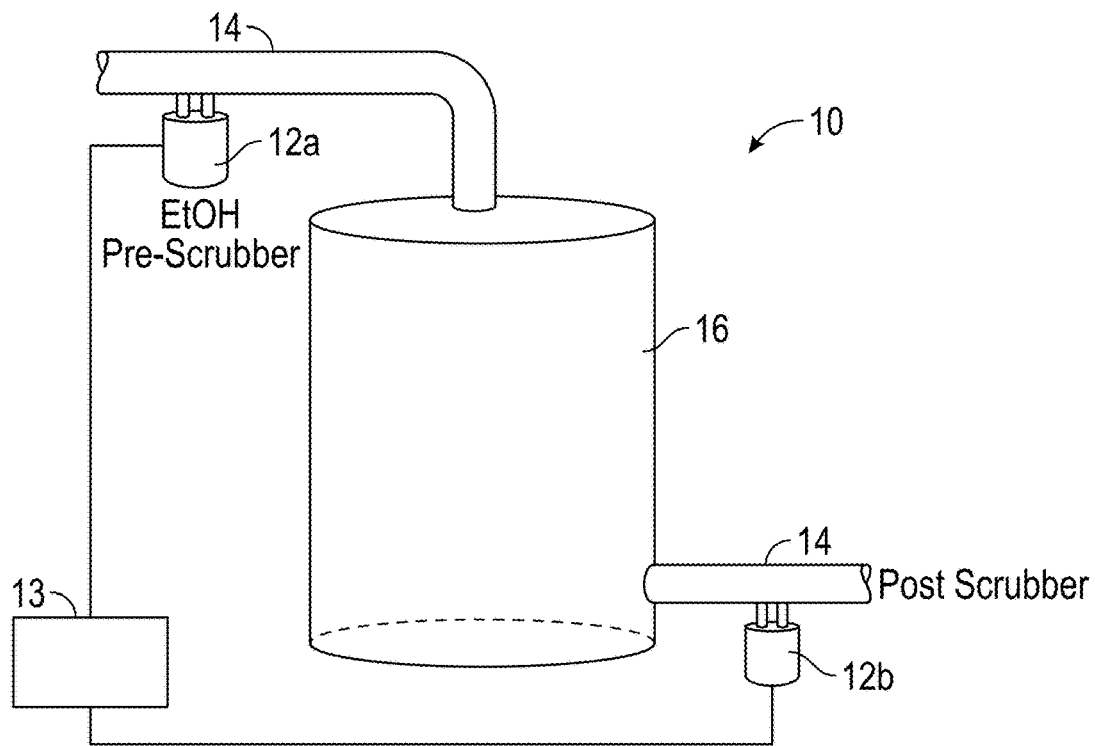
FIG. 1 is a schematic drawing of a system for sensing volatile organic compounds according to the present disclosure.

The present disclosure provides a system and method for detecting volatile organic compounds ("VOCs"). With reference to FIG. 1, a VOC detection system 10 includes one or more sensor assemblies, i.e., first and second sensor assemblies 12a, 12b, which may be coupled to any pipes or conduits 14 carrying gaseous VOCs, i.e., industrial exhaust streams. As shown in FIG. 1, the system 10 may include a scrubber 16, or any other air pollution control device for removing particulates and/or gaseous compounds from industrial exhaust streams. In embodiments, the system 10 may include any other industrial components other than the scrubber 16.

The scrubber 16 is configured to remove certain compounds from the conduit 14, such as the VOCs which the first and second sensor assemblies 12a, 12b are configured to sense. The scrubber 16 may be disposed downstream of an exhaust source (e.g., fermentation tank), which is coupled to the conduit 14. This configuration is commonly used in wineries, breweries, industrial composting facilities, and other industrial exhaust systems, to remove VOCs and other compounds.

Using two or more sensor assemblies 12a, 12b allows for sensing of the VOCs at multiple points in the conduit 14. In particular, the first sensor assembly 12a may be disposed upstream of the scrubber 16 and the second sensor assembly 12b may be disposed downstream of the scrubber 16. This configuration allows for sensing of VOCs and/or detecting concentration of VOCs upstream and downstream of the scrubber 16, allowing for determination of the effectiveness of the scrubber 16. This may be accomplished by comparing the concentrations as measured by the first and second sensor assemblies 12a, 12b and determining effectiveness of the scrubber 16 based on a difference between the concentrations as measured by the first and second sensor assemblies 12a, 12b, respectively.

Each of the first and second sensor assemblies 12a, 12b are coupled to a main computing device 13, which compares the measurements from each of first and second sensor assemblies 12a, 12b to determine the difference between the first and second concentrations. The main computing device 13 may then compare the difference to a predetermined threshold to determine efficiency of the scrubber 16.

The main computing device 13 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

The main computing device 13 and the first and second sensor assemblies 12a, 12b are interconnected to each other using any suitable connection or communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)).

With reference to FIGS. 2-5, a sensor assembly 20, which may be used as the first and second sensor assemblies 12a, 12b, includes a housing 22. The housing 22 may be airtight and may be of any suitable shape, such as cylindrical, rectangular, etc. The housing 22 may be formed from any gas impermeable material such polycarbonate, metal, glass, and the like. The housing 22 is coupled to an inlet assembly 24 and an outlet assembly 26 for sampling gas from the conduit 14 and returning the gas thereto.

The inlet assembly 24 may be coupled to a valve 28, which is in turn coupled to, and controls flow of gases into the housing 22. In embodiments, the valve 28 may be coupled to a standard gas source 30, which supplies a standard of the gas being analyzed for calibration. Thus, in embodiments where ethanol is being analyzed by the sensor assembly 20, the standard gas source 30 supplies gaseous ethanol at a standard concentration.

The valve 28 is also coupled to an air source 32, which may be used for flushing the housing 22 and an analyte gas source 34. The analyte gas source 34 may provide any gaseous composition of one or more constituent gases with a concentration to be analyzed by the sensor assembly 20. In embodiments, the analyte gas source 34 may be coupled to a headspace of a reaction tank, such as a fermentation tank. The gaseous composition contained in the headspace is then supplied to the sensor assembly 20 to measure the concentration of an analyte, which is a constituent of the gaseous composition. The valve 28 may be any multi-directional valve, such as a four-way valve, which serves to couple multiple inputs, namely, the standard gas source 30, the air source 32, and the analyte gas source 34, to the housing 22. The outlet assembly 26 may also include a valve 36, which may be a multi-directional valve, such as a three-way valve, which is coupled to the housing 22, a vent 38, and an outlet 40. The vent 38 may be used to remove any gases from the sensor assembly 20. The outlet 40 is coupled to the conduit 14 and returns the gaseous composition thereto.

The sensor assembly 20 further includes a gas sensor 48 configured to detect VOCs. The sensor assembly 20 may also include a temperature sensor 62, which may be a thermistor. The sensor assembly 20 may further include a relative humidity sensor 64, which may be a hygrometer, configured to measure both moisture and air temperature. The sensor assembly 20 may additionally include a pressure sensor 66, which may be any transducer configured to measure gas pressure within the housing 22. Furthermore, the sensor assembly 20 may also include a light sensor 68 configured to measure light intensity of a light source 70 disposed within the housing 22. The light source 70 is used in conjunction with the gas sensor 48. The light source 70 may be a light emitting diode ("LED") and may emit ultraviolet light at a wavelength from about 320 nm to about 400 nm.

Figure 2:
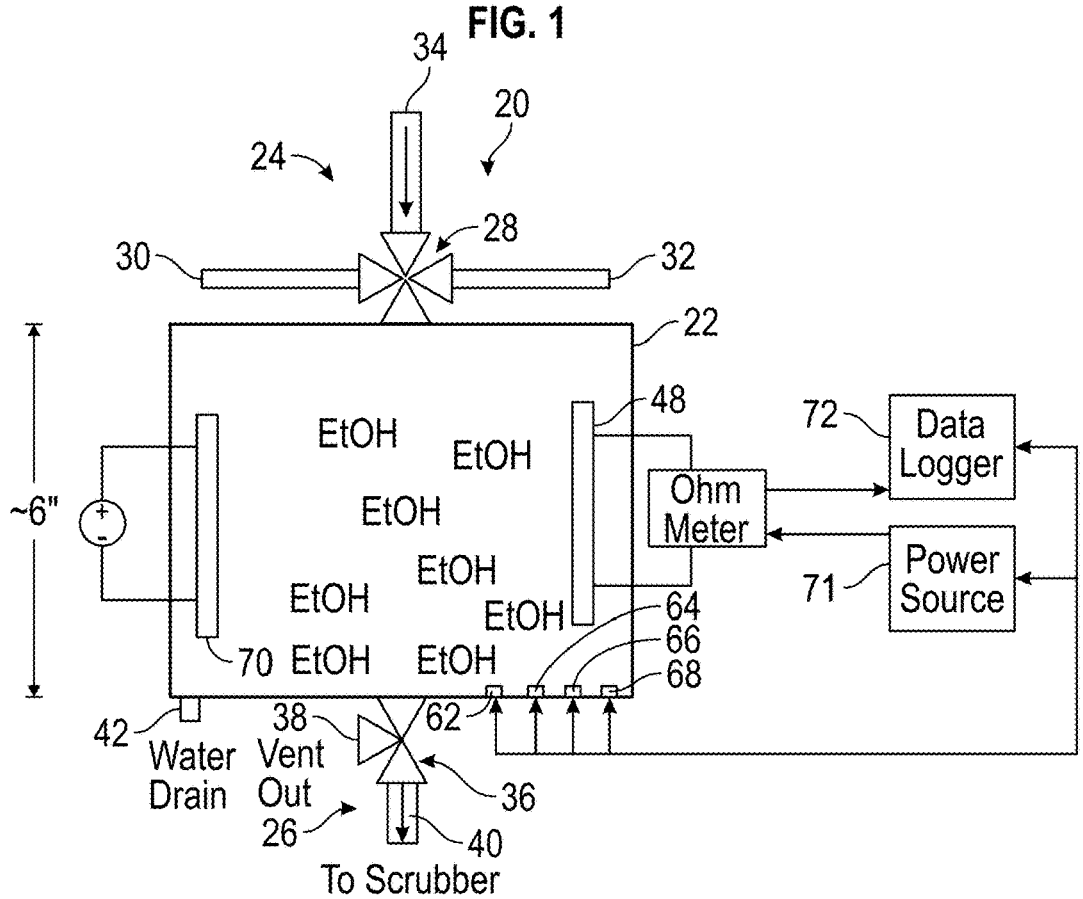
FIG. 2 is a schematic drawing of a sensor assembly of the system of FIG. 1 for sensing volatile organic compounds according to one embodiment of the present disclosure.
Figure 3:
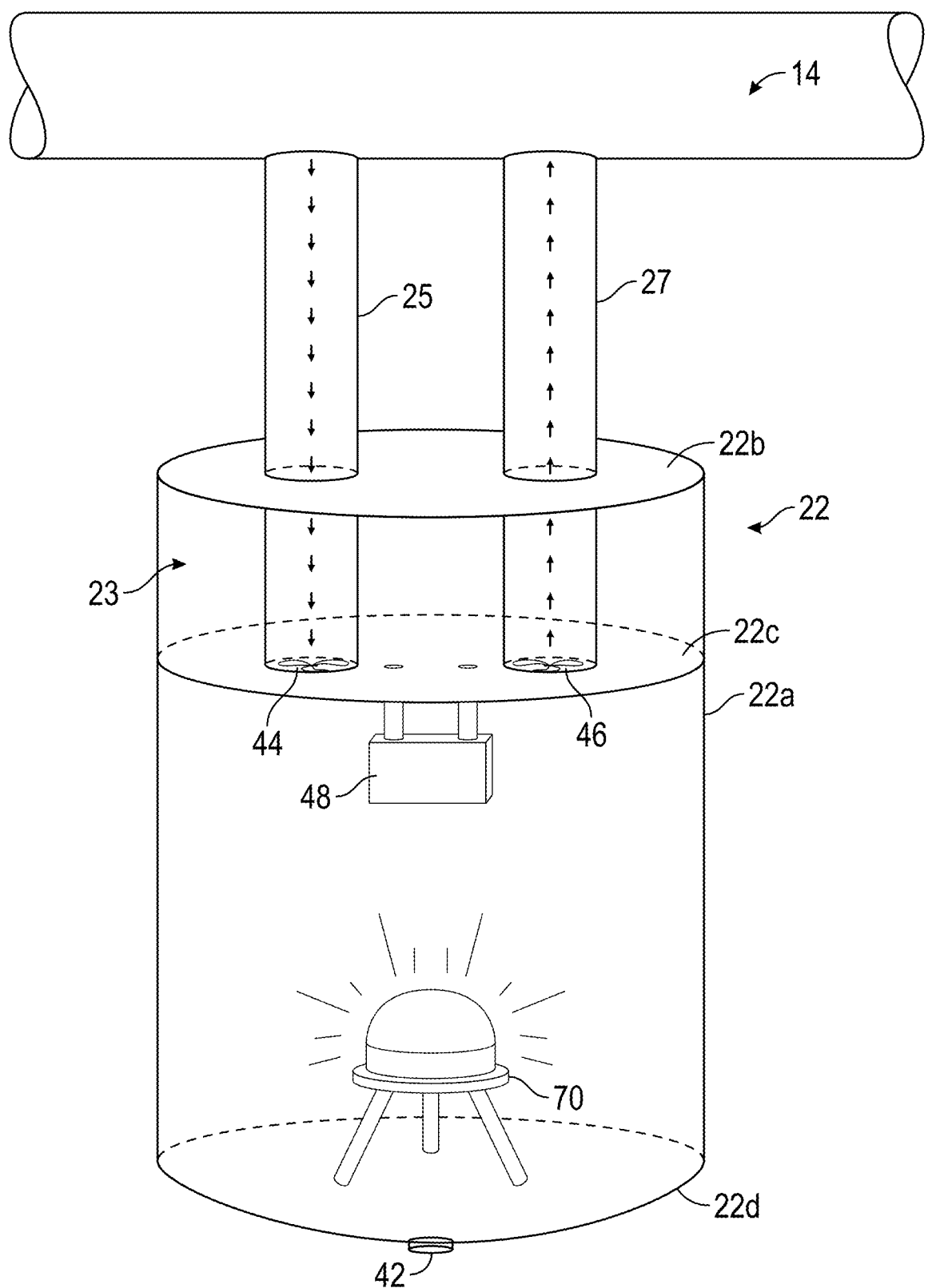
FIG. 3 is a schematic drawing of the sensor assembly of the system of FIG. 2 for sensing volatile organic compounds according to another embodiment of the present disclosure.
Figure 4:
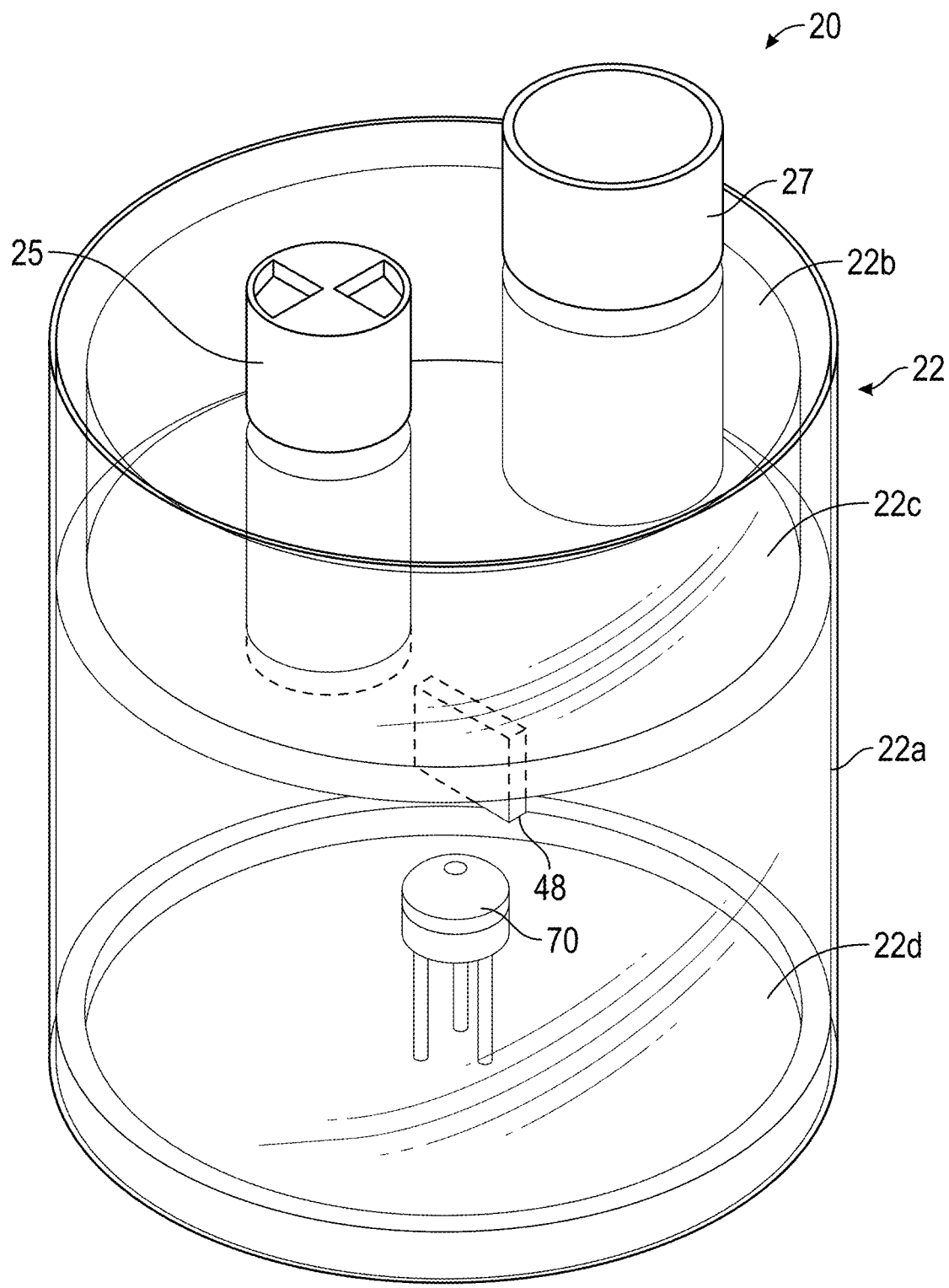
FIG. 4 is a top perspective view of the sensor assembly of FIG. 2.
Figure 5:
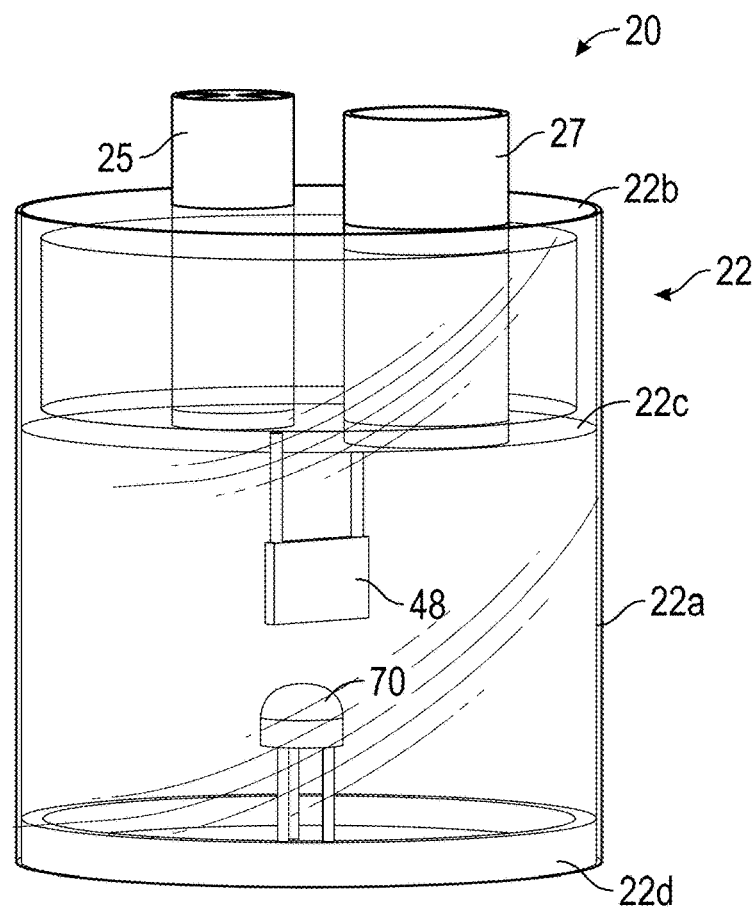
FIG. 5 is a side perspective view of the sensor assembly of FIG. 2.

With reference to FIGS. 3-5, the housing 22 is shown as having a cylindrical side wall 22a having a top wall 22b, an intermediate wall 22c, and a bottom wall 22d. The inlet assembly 24 (FIG. 2) is coupled to the conduit 14 via an intake pipe 25 and the outlet assembly 26 (FIG. 2) is coupled to the conduit 14 via an outtake pipe 27. The intake pipe 25 and the outtake pipe 27 extend from and pass through the top wall 22b. In embodiments, the sensor assembly 20 may be oriented in any configuration relative to the conduit 14, such as laterally, upwardly, downwardly, and the like. The intake and outtake pipes 25 and 27 pass through the top wall 22b and terminate at the intermediate wall 22c. The gas sensor 48, the temperature sensor 62, the relative humidity sensor 64, the pressure sensor 66, and the light sensor 68 (FIG. 2) may be coupled to an inner surface of the intermediate wall 22c, such that the gas sensor 48 and the sensors 62-68 are exposed to the inner volume of the housing 22 into which the gaseous composition is pumped into for analysis.

The top wall 22b and the intermediate wall 22c define a headspace 23 therebetween, which may be used to house additional components associated with the gas sensor 48 and the sensors 62-68, such as wiring, integrated circuit boards, a power source 71, and a computing device 72 (FIG. 2). The computing device 72 is coupled to the gas sensor 48 and the sensors 62-68 and the computing device 72 is configured to collect and store measurements therefrom. The computing device 72 may include the same components as the main computing device 13. In embodiments, the main computing device 13 may be coupled to the gas sensor 48.

Furthermore, the housing 22 may include a drainage opening 42 defined through the bottom wall 22d of the housing. The opening 42 is used to remove condensation accumulated in the housing 22. The drainage opening 42 may have a frustoconical shape which narrows toward the bottom. Condensation may collect within the housing 22 from the water content of the gaseous composition. The drainage opening 42 may also include an airtight plug (not shown) which may be removed to drain any condensate that accumulated in the housing 22.

The housing 22 may be modular such that the cylindrical side wall 22a may be removably coupled to the top wall 22b using clamps or a threaded connection. Similarly, the intermediate wall 22c and the bottom wall 22d may also be removably coupled to the cylindrical side wall 22a. The modular arrangement provides for removal of the intermediate wall 22c and various components attached thereto, such as the gas sensor 48, the sensors 62-68, and the computing device 72.

With reference to FIG. 3, the inlet assembly 24 includes an intake flow control device 44 and the outlet assembly 26 includes an outlet flow control device 46 (FIG. 3) for moving the gaseous composition through the sensor assembly 20. Flow control devices 44, 46 may be any pump or fan suitable for moving gases to and from the conduit 14 through the intake pipe 25 and the outtake pipe 27. The flow control devices 44, 46 operate with the valves 28, 36 to control the flow of the gaseous composition into the sensor assembly 20. In embodiments, the intake flow control device 44 operates until a predetermined pressure set point is reached within the housing 22. After the pressure setpoint is reached, the intake flow control device 44 may be shut off and the valve 28 (FIG. 2) may also be closed. While the gaseous composition is being pumped into the housing 22, the valve 36 (FIG. 2) is closed and the outtake flow control device 46 is also shut off.

Once the housing 22 is filled with the gaseous composition, both the inlet assembly 24 (FIG. 2) and the outlet assembly 26 (FIG. 2) are shut off, i.e., the intake flow control device 44 and the outtake flow control device 46 are shut off and the valves 28 and 36 (FIG. 2) are closed, such that the housing 22 is sealed off from the conduit 14 allowing for the gas sensor 48 to analyze the gaseous composition to determine concentration of the VOCs. After the gas sensor 48 completes its analysis and data is collected by the computing device 72, the outtake flow control device 46 is turned on and the valve 36 is open to release the gaseous composition within the housing 22 back into the conduit 14. The computing device 72 is also coupled to the intake flow control device 44, the outtake flow control device 46, and the valves 28 and 36, such that the computing device 72 controls their operation in a sequence to fill and vent the housing 22. Moreover, the computing device 72 may also activate the gas sensor 48, the sensors 62-68, and the light source 70 to analyze the gaseous composition within the housing 22. In embodiments, the sensor assembly 20 may be operated without any flow control devices or with only one flow control device (i.e., the intake flow control device 44 or the outtake flow control device 46). Accordingly, if there the gaseous composition entering the sensor assembly 20 is under sufficient positive pressure then the valves 28 and 36 may be opened to fill and vent the sensory assembly 20 either manually or under control by the computing device 72.

Figure 6:
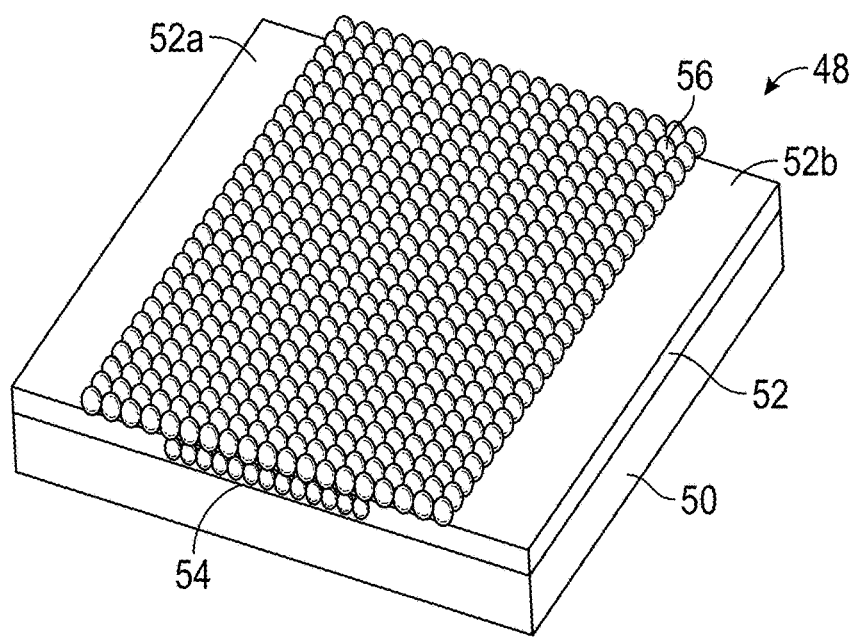
FIG. 6 is a perspective view of a gas sensor of the sensor assembly of FIGS. 2-5 according to one embodiment of the present disclosure.

With reference to FIG. 6, the gas sensor 48 is a metal oxide nanostructure sensor. The gas sensor 48 includes a substrate 50, which may be formed from any dielectric material such as glass, polyethylene terephthalate, and the like. The gas sensor 48 includes a conductive coating 52, which may be an indium tin oxide (ITO) coating having a resistivity from about 10 Ω/cm to about 50 Ω/cm. The conductive coating 52 may have a thickness from about 50 nm to about 250 nm, in embodiments, from about 100 nm to about 200 nm. The conductive coating 52 includes a channel 54 having a metal oxide nanostructure layer 56 disposed therein.

In embodiments, the nanostructure layer 56 may include zinc oxide ("ZnO") nanostructures. The conductive coating 52 may be etched using any suitable process, such as laser ablation, chemical etching, and the like to form the channel 54, which is bordered by electrodes 52a and 52b formed from the conductive coating 52. The channel 54 may have a width from about 1 mm to about 20 mm, in embodiments from about 5 mm to about 10 mm. The substrate 50 may have any suitable shape, such as, rectangular, for accommodating the channel 54. ZnO nanostructures include nanoparticles (see insets of FIGS. 13A-C) having a diameter from about 15 nm to about 30 nm, which in embodiments may be from about 20 nm to about 25 nm.

After the channel 54 is formed, the nanostructure layer 56 may be formed using a drop-casting method. The nanostructure layer 56 may be formed from nanoparticles having a size up to about 10 μm or nanotubes having a width from about 50 nm to about 200 nm and a length from about 50 nm to about 5 μm. In a drop-casting method, ZnO nanostructures are uniformly dispersed in deionized (DI) water to produce a thin slurry. Thereafter, slurry drops having a volume of about 8 μL are dropped onto the channel 54 between the electrodes 52a and 52b. The substrate 50 may then be kept at about 120° C. for about 2 hours to vaporize DI water, to form the nanostructure layer 56.

Figure 7:
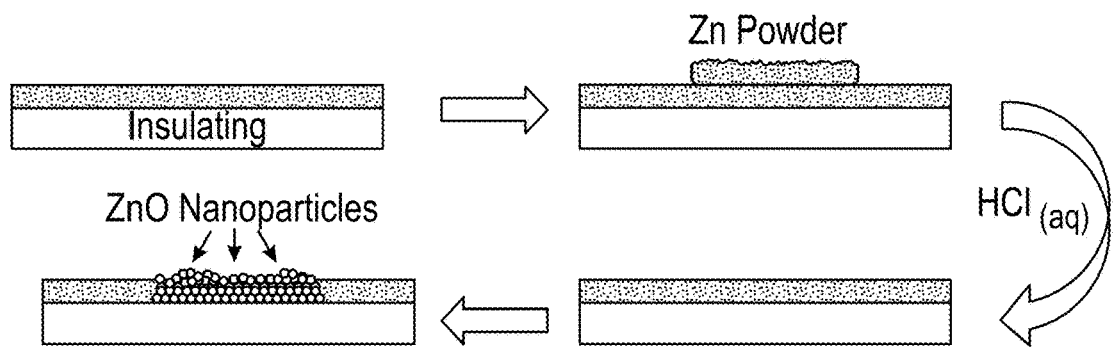
FIG. 7 is a schematic drawing of a method for forming the sensor of FIG. 6.

With reference to FIG. 7, the nanostructure layer 56 may be formed using an alternate method in which zinc metal powder is disposed over the conductive coating 52. The zinc metal powder and the conductive coating 52 are treated with a hydrochloric acid aqueous solution at a concentration of about 1 mol/L, which forms the channel 54. Thereafter, ZnO nanostructures are deposited in the channel 54 to form the nanostructure layer 56.

Figure 14A:
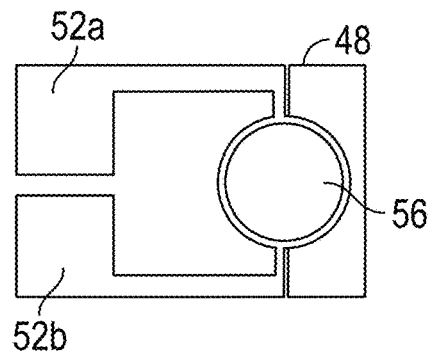
FIG. 14A is top view of a gas sensor according to another embodiment of the present disclosure.

FIG. 14A shows another embodiment of the gas sensor 48. The nanostructure layer 56 may be deposited as any suitable shape, such as a circle with two electrodes 52a and 52b extending therefrom. A technique for depositing the nanoparticles between two electrodes 52a and 52b is also disclosed. ZnO nanostructures may be mixed with a mixture ethyl cellulose, alpha terpineol, and ethanol to form a nanoparticle paste. The paste may be then applied using a mask (not shown), which may be a layered structure formed from adhesive tape, covering/masking the electrodes 52a and 52b. The mask may have a predetermine thickness which provides a desired thickness to the nanostructure layer, which may be from about 0.1 mm to about 0.5 mm. The mask includes an opening corresponding to a desired shape of the nanostructure layer 56, such as a circular opening, thereby leaving the circular region of the gas sensor 48 including portions of the electrodes 52a and 52b uncovered. Thus, when the paste is applied through the opening, the nanostructure layer 56 is formed within the opening. Excess paste may then be scraped off such that the paste that is confined to the circular region at a thickness equivalent to the thickness of the mask. After the application of the ZnO nanostructures, the gas sensor 48 is heated to a temperature from about 400° C. to about 500° C. for about 1 hour or any other suitable time period in a furnace and allowed to cool (FIG. 14B) to remove hydrocarbons from the paste and leave behind the nanostructure layer 56.

In additional embodiments, the nanostructure layer 56 may be subjected to annealing. It is envisioned that crystallinity of the nanostructures of the nanostructure layer 56 may have substantial influence on several key sensing parameters, including, but not limited to, sensitivity towards VOCs, selectivity of the signal towards various VOCs, and stability of the nanostructures towards degradation. These sensing parameters may be increased by annealing the nanostructure layer 56 at a temperature from about 200° C. to about 600° C., in embodiments, from about 300° C. to about 500° C.

Effective surface area of the nanostructures of the nanostructure layer 56 is another parameter that may be adjusted to increase sensitivity of the nanostructure layer 56. Increased surface area provides increased access to VOC gases, which affects the detection limits and overall current response of the gas sensor 48. A wet-chemical etching process may be used to increase the surface area. In embodiments, ammonia and cetyltrimethylammonium bromide may be used to enhance ZnO nanostructure surface area by increasing surface roughness at mild etching conditions and creating pores and/or hollowing out the structures under more extreme etching conditions. Additionally, any defects, either oxygen vacancies or nitrogen doping, created by this etching process also enhances the absorption of light and broaden the wavelength range, which can be utilized to achieve sensing activity.

The gas sensor 48 operates based on reactive oxygen species production and ethanol oxidation on the surfaces of the nanostructures, i.e., ZnO nanostructures, of the nanostructure layer 56 under UV irradiation, which leads to a decrease in resistance in the presence of VOCs, i.e., ethanol gas compared to that in air. In particular, when ZnO nanostructures of the nanostructure layer 56 are exposed to air in the dark, the adsorbed oxygen molecules trap electrons from the conduction band of ZnO, resulting in the presence of a low-conductivity depletion region in the surface layer and narrowing the conduction channels in ZnO nanostructures as illustrated by the reaction (I):

$$O_2^-, \text{ i.e., } (O_2 + e^- \rightarrow O_2^-) \tag{I}$$

Due to the large adsorption energy, oxygen ions ($O_2^-$) are thermally stable and difficult to remove from the ZnO surface at room temperature. As such, the ZnO nanostructures cannot react with ethanol molecules and have a poor gas sensing response in the dark. When the ZnO nanostructures of the nanostructure layer 56 are illuminated with UV light, the photo-induced electron-hole pairs are generated in ZnO nanostructures due to the larger photon energy than the band gap of ZnO (of about 3.2 eV). Some of the photo-induced electron-hole pairs desorb the adsorbed oxygen ions on the surface as illustrated by the following reaction (II) below, resulting in a reduction in the depletion layer depth and an increase in the free carrier concentration, which in turn, increases photocurrent in response to the UV light from the light source 70.

$$h^+ + O_2^- \rightarrow O_2 \tag{II}$$

With the raised free carrier density, the ambient oxygen molecules react with the photo-generated electrons, creating a new photo-induced chemisorption oxygen molecules as illustrated by the following reaction (III):

$$O_2 + e^-(h\nu) \rightarrow O_2^-(h\nu)$$

Unlike the chemisorbed oxygen ions which are strongly attached to the surface of the ZnO nanostructures, these photo-generated oxygen ions [$O_2^-$ (hv)] are weakly bound to ZnO nanostructures and can be easily removed when exposed to UV light at room temperature. Thus, when the gas sensor 48 is exposed to VOC, e.g., ethanol, these additional adsorbed oxygen molecules on the surface of ZnO nanostructures react with ethanol molecules as the following reactions: $C_2H_5OH + 3O_2^-$ (hv) $\rightarrow 2CO_2 + 3H_2O + 3e^-$, which release electrons back to the conduction band of ZnO nanostructures. This decreases the surface depletion layer depth and increases electrical conductivity of the nanostructure layer 56. In other words, the signal response increases when the gas sensor 48 is exposed to VOCs. The gas sensor 48 produces a signal that is proportional to the air mixing ratio of VOCs and is sensitive down to sub-ppm levels.

In view of the above-described reaction mechanism, the presence of VOCs gas, such as ethanol, greatly lowers the resistance of the nanostructure layer 56. This is consistent with the production of reactive $O_2$ ions on the surface of the ZnO nanostructures of the nanostructure layer 56 when exposed to UV irradiation, which subsequently oxidize adsorbed VOC molecules. As such, the change in resistance is used to measure the amount of VOCs in the gaseous composition. The gas sensor 48 may be coupled to an ohm meter 74 (FIG. 2). In particular, the ohm meter 74 is coupled to the electrodes 52a, 52b and measures the resistance of the gas sensor 48. The change in resistance is correlated to the amount of the VOCs is determined by the computing device 72.

Figure 8:
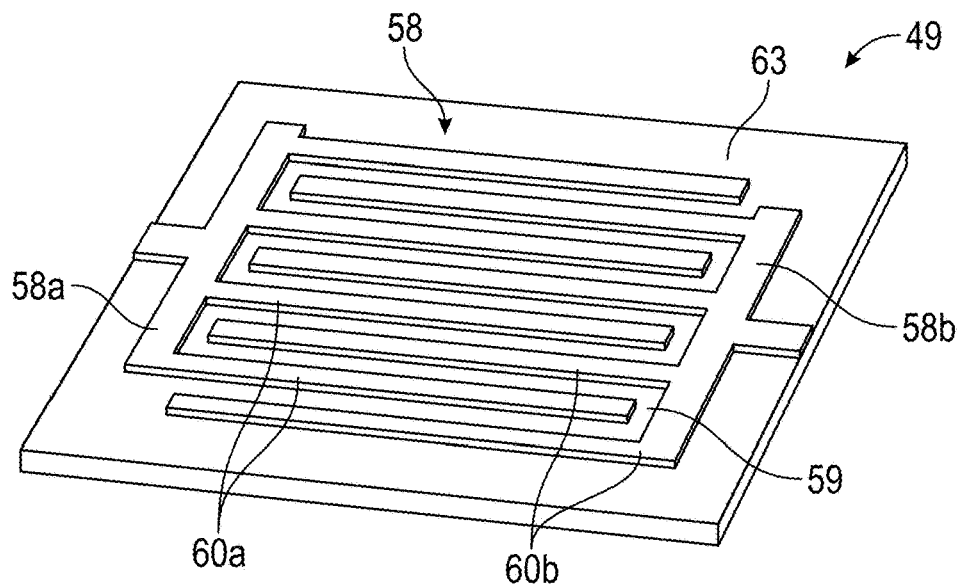
FIG. 8 is a perspective view of a sensor of the sensor assembly of FIGS. 2-5 according to another embodiment of the present disclosure.

With reference to in FIG. 8, another embodiment of a gas sensor 49 is shown, in which the conductive coating 52 is formed as an interdigitated circuit 58 having a first electrode pattern 58a and a second electrode pattern 58b disposed on a substrate 63, such that a plurality of finger electrodes 60a and 60b of each of the electrode patterns 58a and 58b interlock with each other forming a channel 59 having a tortuous pattern that is bound by the electrode patterns 58a and 58b. The electrode patterns 58a and 58b and the channel 59 may be formed in the same manner described above with respect to the electrodes 52a, 52b and the channel 54. The slurry of ZnO nanostructures may be drop-cast onto preformed interdigitated electrode patterns 58a and 59b and/or used to form the patterns directly on the substrate 63. Utilizing a plurality of finger electrodes 60a, 60b divides one large electrode, i.e., electrodes 52a, 52b, into a plurality of n parallel electrodes, which in turn results in a drop in resistance drops as $n^2$, where n is the number of electrodes and an increase in sensitivity by a factor of about 1000.

In further embodiments, prior to drop-casting on the electrode patterns 58a and 58b, the ZnO nanostructures is suspended in an aqueous solution of ammonia at a concentration of about 0.5% and cetyl trimethylammonium bromide at a concentration of about 0.8%. The solution is gently stirred at room temperature (i.e., from about 20° C. to about 25° C.) for up to about 8 hours, during which the ZnO nanostructures are slowly etched by the ammonia. The role of the CTAB is to control the kinetics of this etching process by passivating the lateral surfaces of the rod nanostructures and thereby slowing their etching rate. This causes preferential etching at the tips of the rod nanostructures resulting in hollowing of the rod structures and converting them to nanotubes. These nanotubes afford a marked increase in surface area as the inner walls are available for VOC adsorption, further enhancing the sensitivity of the ZnO nanostructures.

Sensor design and operating parameters of the gas sensor 48 can be easily controlled to change the response characteristics. In this way the gas sensor 48 is extremely flexible to the specifics of the application. Its low cost and rugged design means that the gas sensor 48 can be deployed in an environment high in water vapor and contaminants. The gas sensor 48 may be used to obtain near-continuous data since the action of the light source 70 oxidizes any solid buildup that might accumulate on the surface of the gas sensor 48, avoiding surface deactivation which results in loss of sensitivity over time. It is also worth noting that the LEDs for making the light source 70 are a simple, low-cost, and environmentally friendly alternative to typical sensor designs which involve elevated temperatures or large applied voltages. Furthermore, the ZnO nanostructures the gas sensor 48 are cheap and commercially available, making large-scale sensor models extremely cost-effective.

The following Examples illustrate embodiments of the present disclosure. These Examples are intended to be illustrative only and are not intended to limit the scope of the present disclosure. Also, parts and percentages are by weight unless otherwise indicated. As used herein, "room temperature" or "ambient temperature" refers to a temperature from about 20° C. to about 25° C.

EXAMPLES

Example 1

This example describes fabrication of a metal oxide nanostructure sensor.

Figure 9:
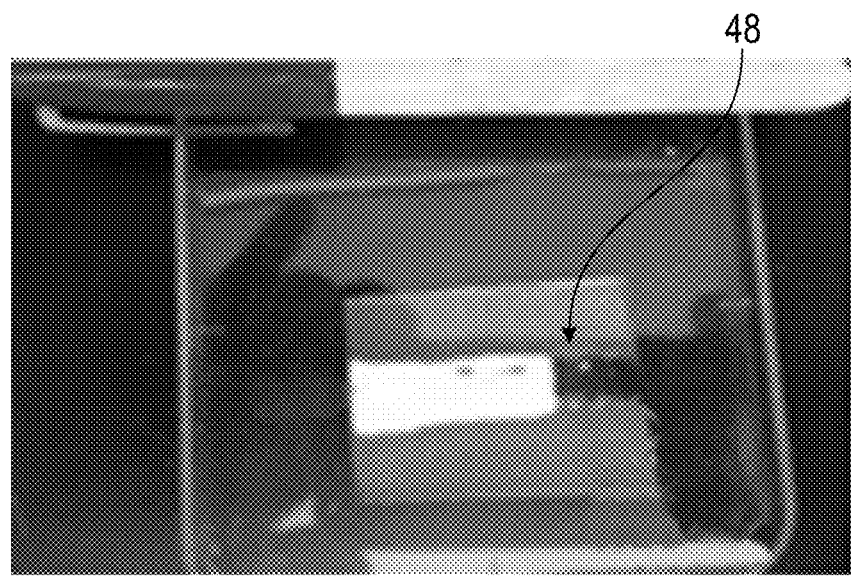
FIG. 9 is a photograph of a gas sensor having a zinc oxide nanostructure layer disposed on an indium tin oxide (ITO) coating glass substrate according to the present disclosure.

A polyethylene terephthalate ("PET") substrate coated with ITO (thickness of about 180 nm) having resistivity of about 35 Ω/square on one side surface was used for making a gas sensor. The ITO coating was etched by laser ablation to remove a strip of the conducting coating to form parallel electrodes. The channel width between the two parallel electrodes was about 1 cm, each ITO electrode area was about 35 mm$^2$. ZnO nanostructures having an average diameter of about 40-100 nm, were uniformly dispersed in deionized (DI) water to produce a thin slurry. Multiple drops, each being about 8 μL, of the slurry were dropped on the channel between parallel electrodes, and then kept at approximately 70° C. for about 2 hours to vaporize DI water to fabricate the ZnO nanostructure sensor as shown in FIG. 9.

The sensor was then connected to a multimeter and suspended in a jar with a gas port. A UV (about 365 nm wavelength) LED light source (about 100 W) was held about 5 cm away from the sensor and was turned on to expose the sensor to UV light. To measure the effect of adding ethanol gas, about 10 mL of liquid ethanol was added to the jar, which was heated to about 100° C. using a hot plate placed below the jar. This immediately vaporized the ethanol, and the mixing ratio of ethanol in air was calculated.

Figure 10:
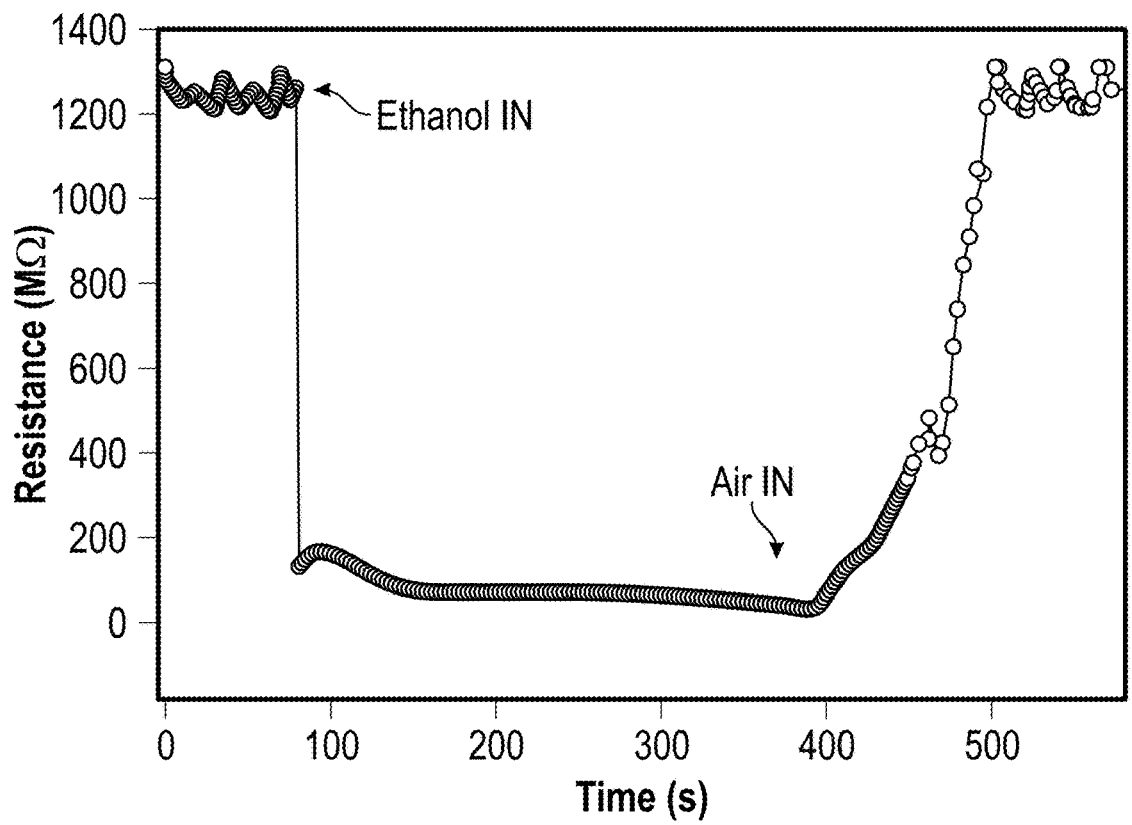
FIG. 10 is a plot of resistance as a function of time of the gas sensor of FIG. 9 when exposed to ethanol gas.

A time series of resistance measurements across the sensor showing the effects of ethanol and air were collected as illustrated by a plot in FIG. 10. The plot of FIG. 10 illustrates that the presence of ethanol gas greatly lowers the resistance of the device. This is consistent with the production of reactive $O_2^-$ ions on the surface of the ZnO nanostructures upon UV irradiation, which subsequently oxidize adsorbed ethanol molecules. After a stable resistance of about 50 NM was observed at approximately 3 minutes, the chamber was flushed with air at about 6.5 minutes, and the resistance returned to baseline levels of about 1250 MΩ approximately 2 minutes later.

The response of the ZnO nanostructure sensor was defined as Ro/REtOH, which is the ratio of the resistance of the sensor in air to the resistance of the sensor in ethanol gas under UV irradiation. The Ro/REtOH values that were observed were always approximately above 1 indicating that the ZnO nanostructure coating was more conductive in the presence of ethanol than in air.

Figure 11:
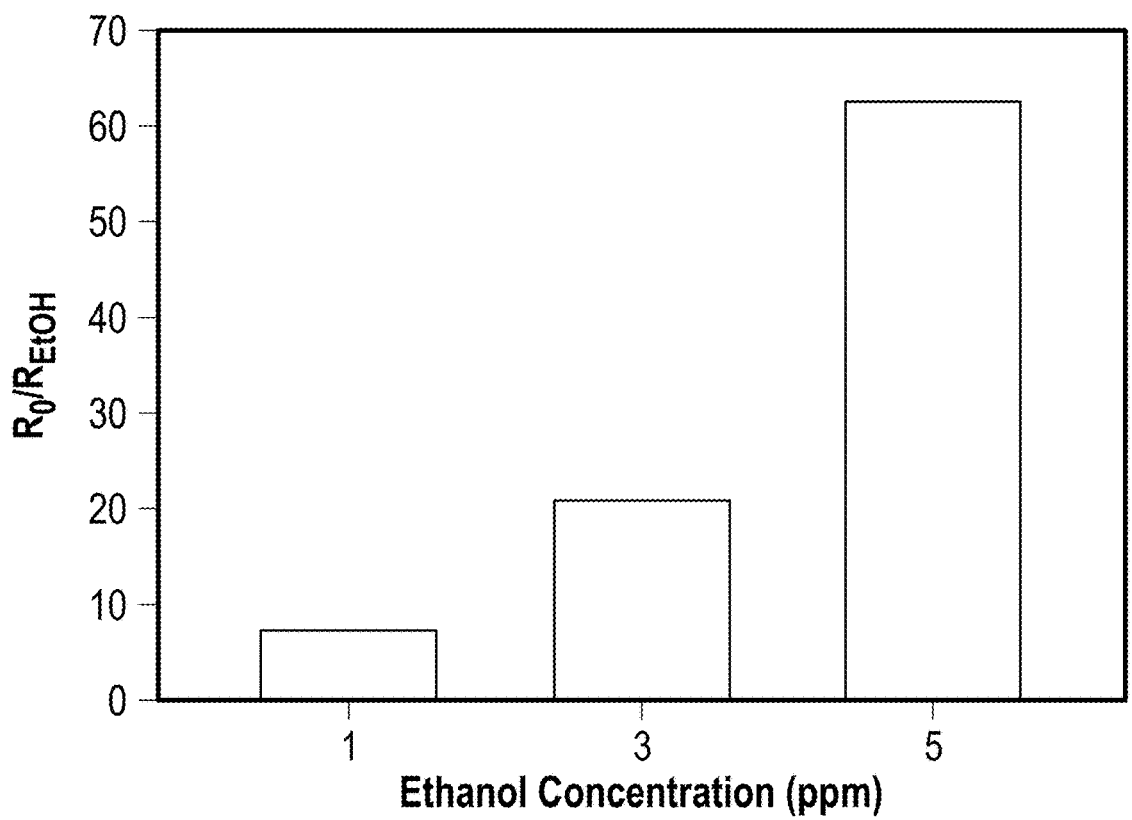
FIG. 11 is bar graph of ratio of the resistance of the gas sensor of FIG. 9 in air to the resistance of the gas sensor in ethanol gas from about 5 ppm to about 70 ppm.
Figure 12:
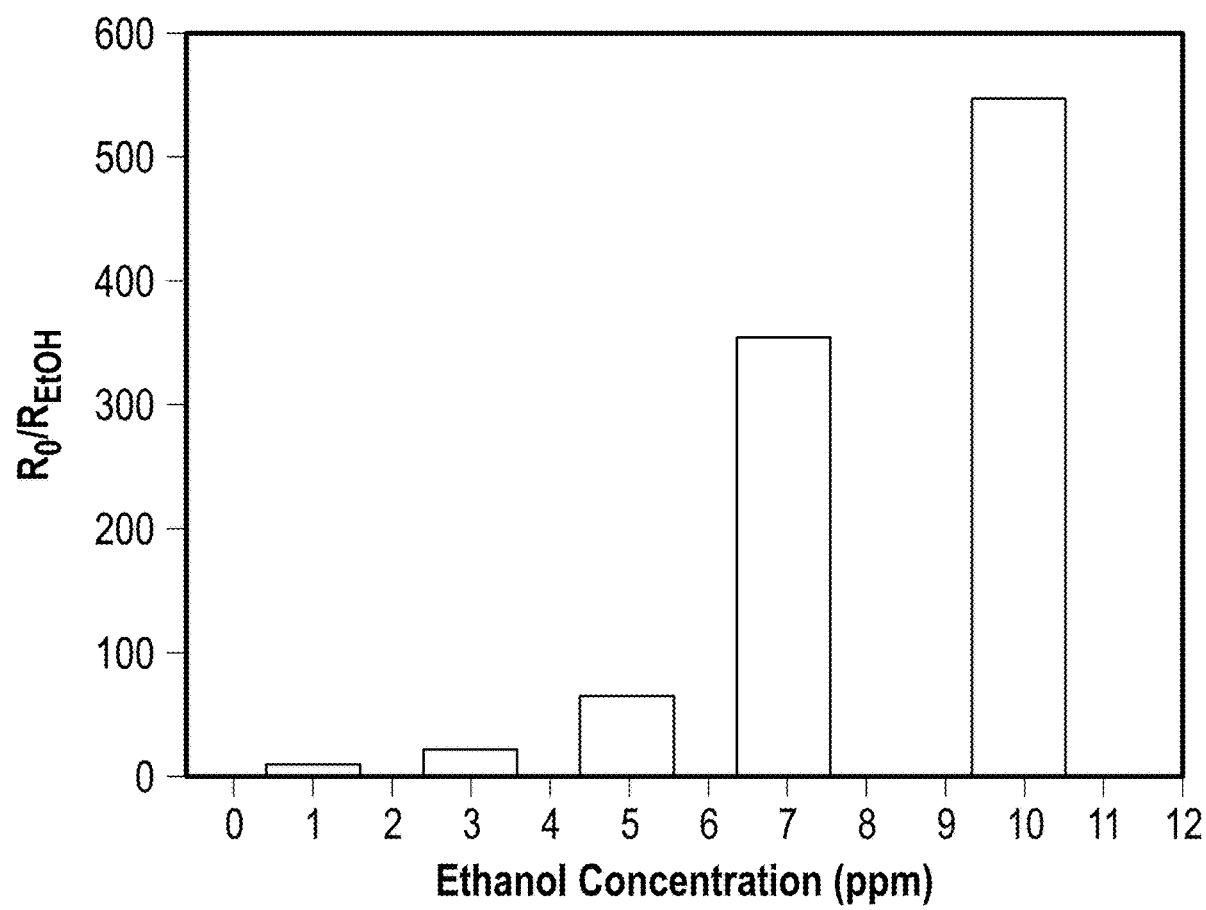
FIG. 12 is bar graph of ratio of the resistance of the gas sensor in FIG. 9 in air to the resistance of the sensor in ethanol gas from about 5 ppm to about 600 ppm.

The sensor response (Ro/REtOH) increased positively with increasing concentrations of ethanol gas as shown in FIGS. 11 and 12. At ethanol concentrations below about 5 ppm, down to about 0.5 ppm or lower, the sensor appeared to behave linearly (FIG. 11). At concentrations approximately above 5 ppm the behavior was more non-linear (FIG. 12).

Example 2

Figure 13A:
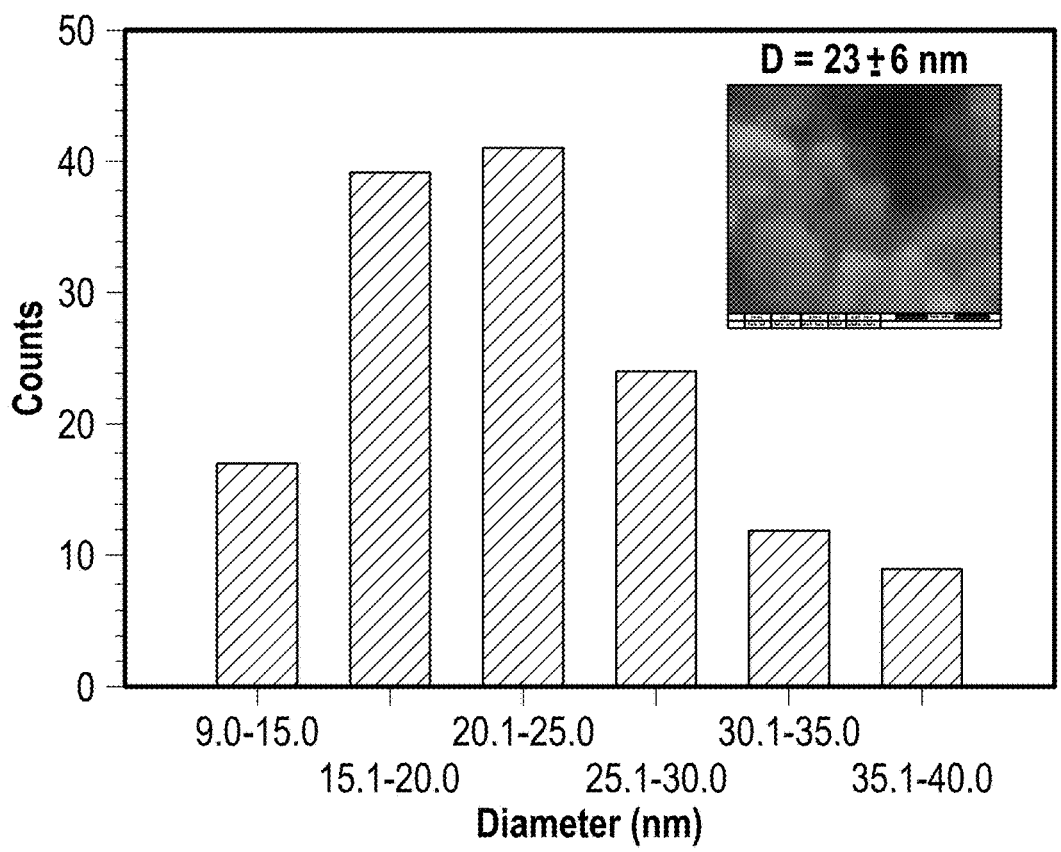
FIGS. 13A-C is a set of histograms and insets of scanning electron microscope (SEM) images showing distribution and shape for zinc oxide (ZnO) nanostructures according to the present disclosure.
Figure 13B:
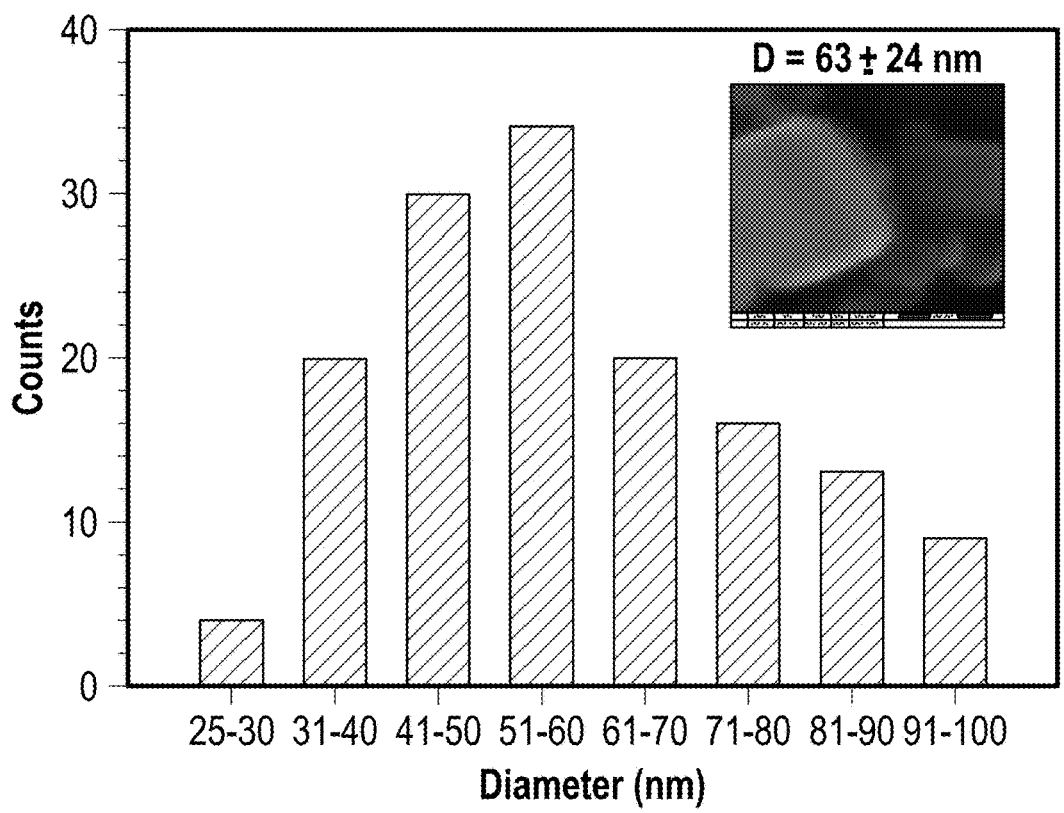
Figure 13C:
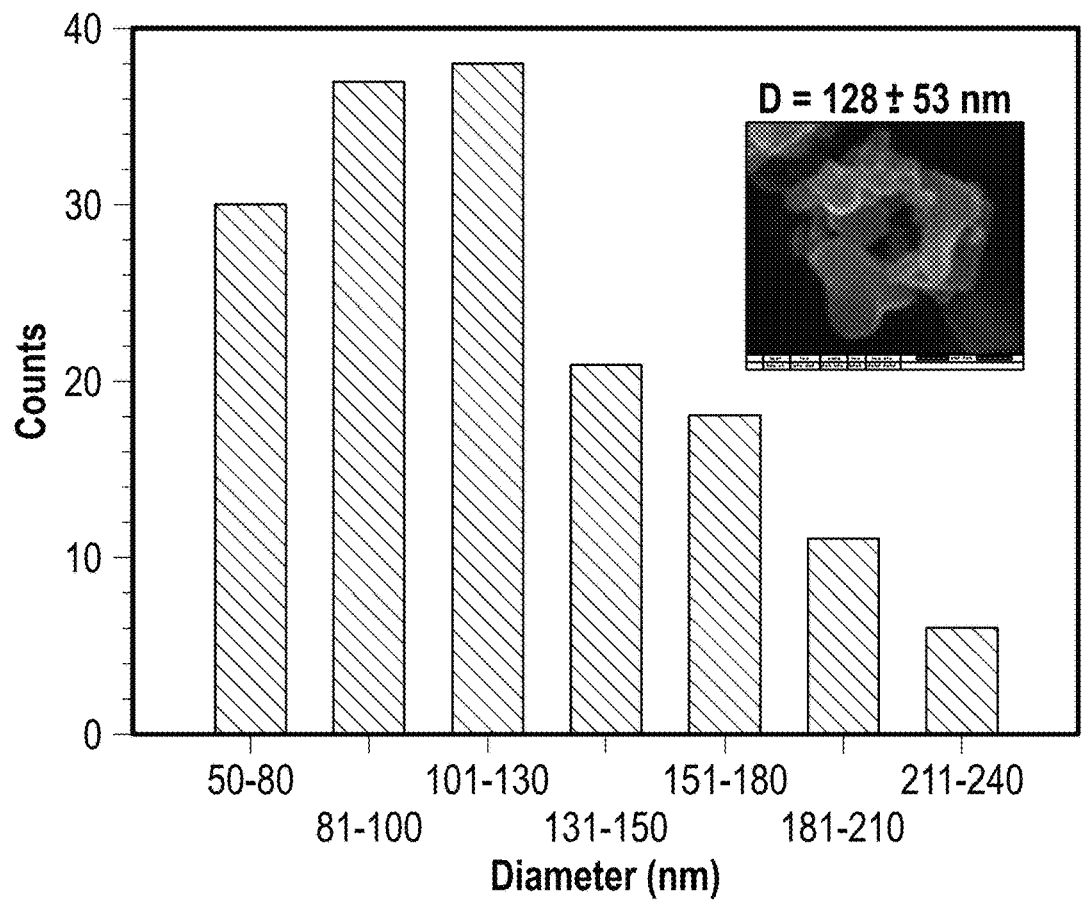

This example describes ZnO nanostructures disposed on the sensor for sensing ethanol and other VOCs Disclosed are the use of different ZnO nanostructures and their stability and response to ethanol. The nanostructures differ in terms of size distribution. Scanning electron microscopy (SEM) was used to image the resulting structures, and histograms depicting size distributions for these samples, as well as a representative electron micrograph are shown in FIGS. 13A-C. Examined ZnO nanostructures have a size range of 23 nm±6 nm, 63±24 nm, and 128±53 nm.

Figure 14B:
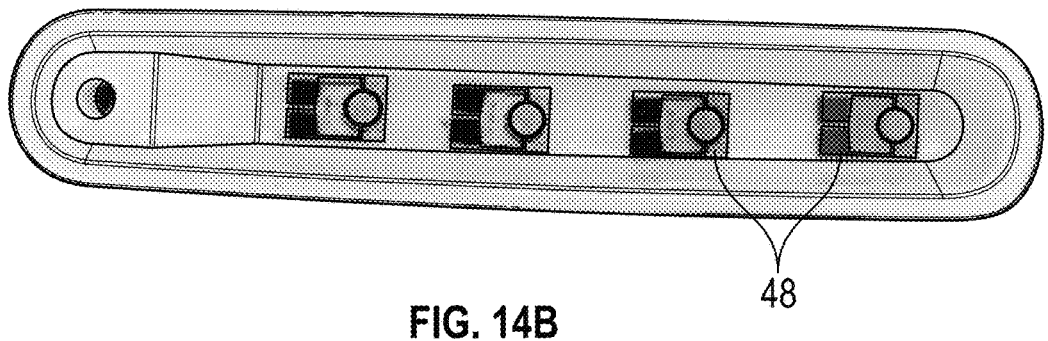
FIG. 14B is a photograph showing ZnO nanostructures applied to interdigitating electrodes (IDE's) of the gas sensors of FIG. 14A.

A new technique for depositing the nanoparticles onto the interdigitated electrodes (IDEs) is disclosed. One gram of ethyl cellulose (49% w/w) is mixed with 6 ml of alpha terpineol and 5 mL of ethanol to form a clear paste, which is then mixed with 10 mg of the ZnO nanostructures. The paste was then applied to a structure made up of a double layer of adhesive SCOTCH® tape covering an IDE. The tape layers included a hole leaving the circular region of the IDE (including the gold finger electrodes) uncovered by the tape. Excess paste was scraped off with a blade such that the paste that was confined to the circular finger electrode region of the IDE at a thickness equivalent to two layers of tape. After the application of the ZnO nanostructures, the IDEs were heated to about 450° C. for approximately 1 hour in a furnace and allowed to cool (FIG. 14B). This removed all traces of hydrocarbons from the paste and left behind a durable coating of nanoparticles on the IDE.

The prepared IDEs were then installed in the housing and then exposed to dry air/ethanol flow within the chamber and also to UV light (nominal 365 nm, 3 W). The air and ethanol standard flow rates were measured with mass flow meters calibrated with a primary source bubble flow meter. Dry air flows of 1 to 4 liters per minute were used to dilute smaller flows (5-200 mL/min) of ethanol gas with NIST-certified concentrations between 103 and 272 ppm. This produced air/ethanol mixtures ranging in concentration from about 0.1 to 10 ppm inside the air chamber where the ZnO sensor was located. A typical experiment with ethanol standards involves a warm up time of about 15 minutes to get a sufficiently flat baseline from the sensor, followed by additions of known amount of ethanol gas into the air stream. The ethanol additions produce a drop in the resistance across the sensor. This was measured with an ohmmeter. This is consistent with a current model of sensor operation: i.e. an oxidizible gas produces excess electrons in the presence of UV light and these decreases the resistance across the sensor.

Figure 15:
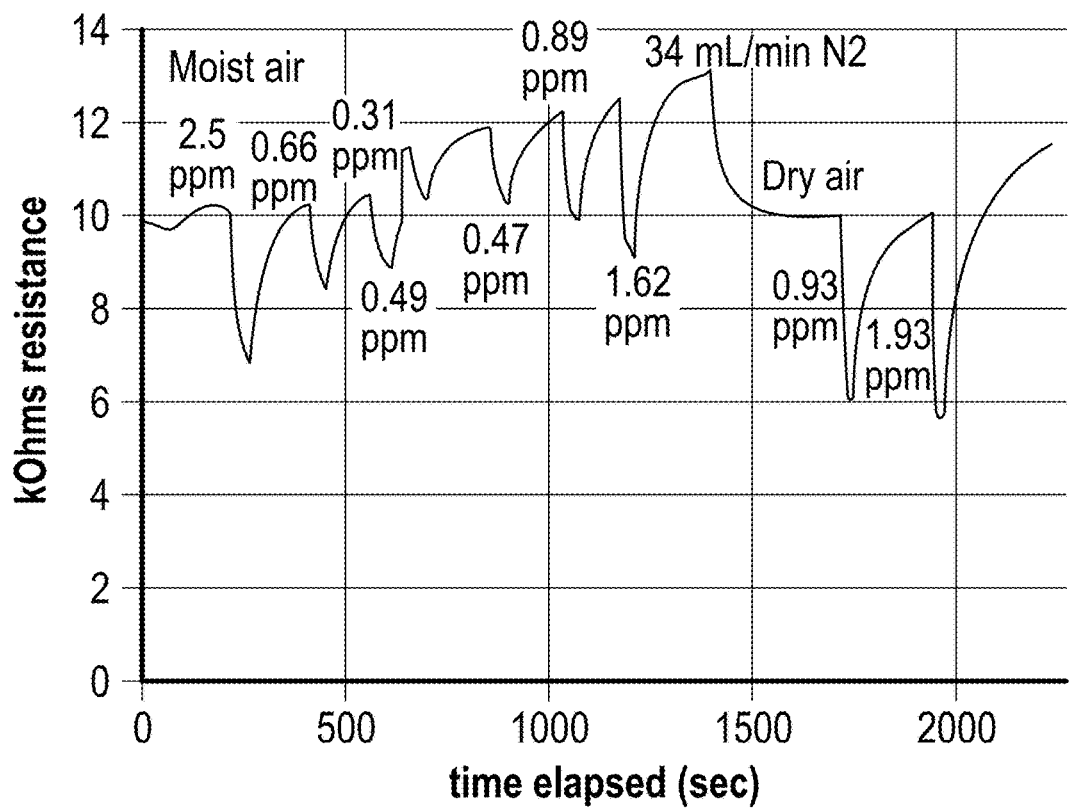
FIG. 15 is a trace showing resistance of the gas sensor of FIG. 14A in response to the indicated amount in parts per million (ppm) of ethanol, nitrogen, moist, or dry air.

FIG. 15 shows the raw data from a typical experiment with the concentration of ethanol indicated (dry air and $N_2$ were also included). Note that the addition of $N_2$ did not cause an appreciable change in the resistance of the sensor. This is important because the ethanol standards are provided in $N_2$, indicating the decrease in resistance across the sensor is due to the presence of ethanol vapor and no other components of the gas stream. A difference in resistance between dry and moist air was observed, suggesting that it is important to maintain the relative humidity of the input air.

Figure 16A:
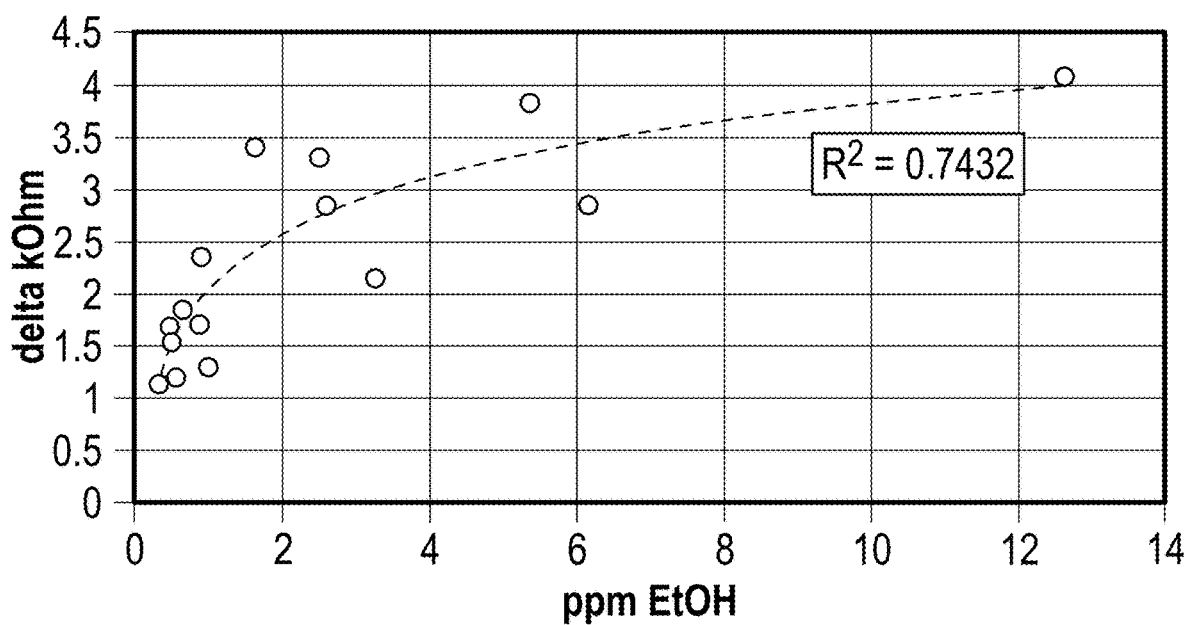
FIG. 16A is a standard response curve of resistance in response to ethanol contacting the sensor of FIG. 14A.
Figure 16B:
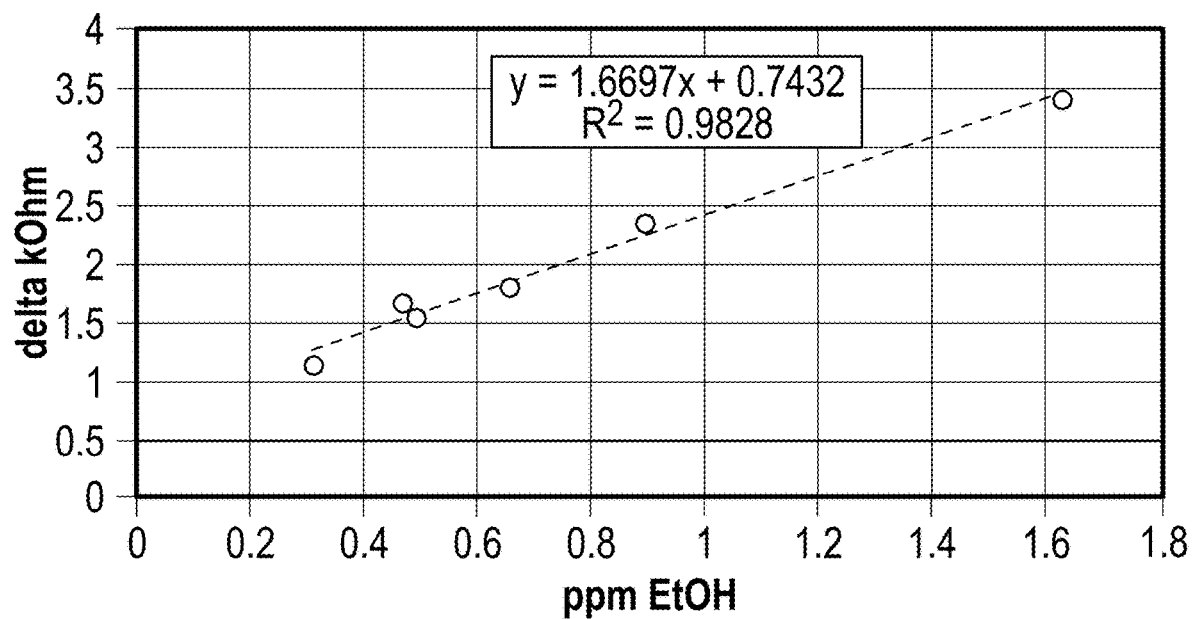
FIG. 16B is a standard response curve of resistance in response to ethanol contacting the sensor of FIG. 14A.
Figure 16C:
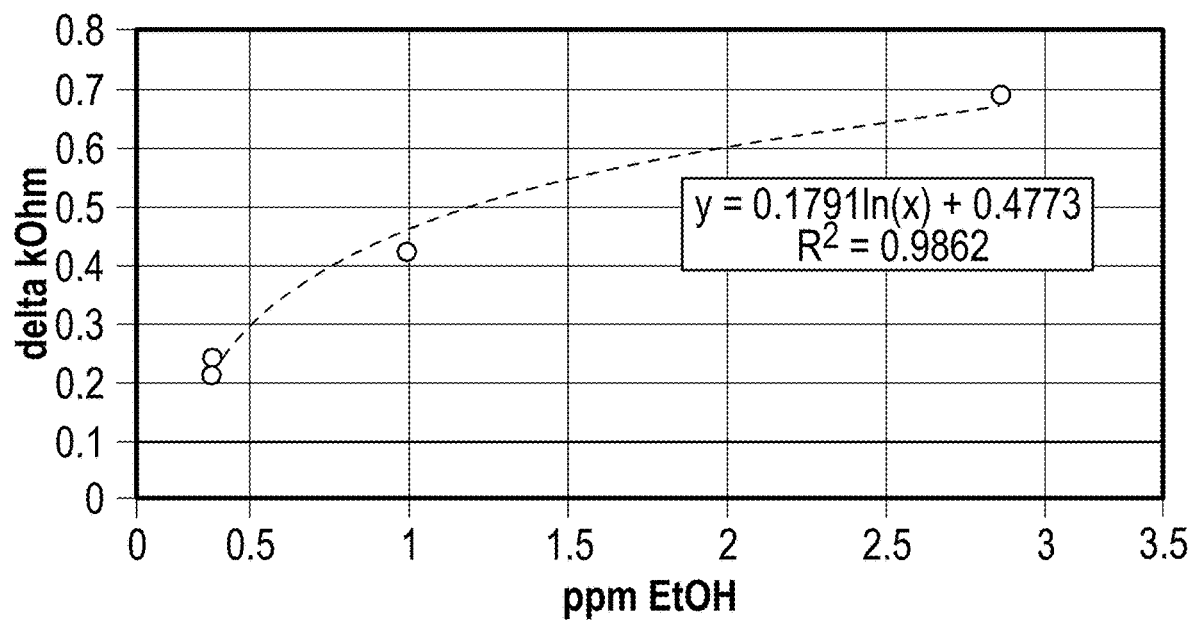
FIG. 16C is a standard response curve f of resistance in response to ethanol contacting the sensor of FIG. 14A.

FIGS. 16A, 16B, and 16C show the standard response curves from three different typical experiments using the 23 nm±6 nm ZnO particles. The sensitivity appears to be excellent, with a linear response down to 300 ppb (FIG. 17B). However, the sensor response appears to be non-linear at concentrations above 2-3 ppm. The significance of these results is that the sensor is reproducible to within about 10% and sensitive to at least two orders of magnitude of ethanol concentrations in samples of moist air. These results are sufficient for measurements at, for example, a winery facility.

It will be appreciated that of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, or material.

What is claimed is:

1. A gas sensor assembly comprising:
a housing;

an inlet assembly configured to carry a gaseous composition having a volatile organic compound into the housing;
an outlet assembly configured to carry the gaseous composition from the housing;
an ultraviolet light source disposed within the housing; and
a gas sensor disposed within the housing and configured to sense an amount of the volatile organic compound, wherein the gas sensor includes:
a substrate;
a conductive coating disposed on a surface of the substrate having a channel defined in the conductive coating; and
a metal oxide nanostructure layer disposed within the channel, the metal oxide nanostructure layer having a resistance, which varies in response to contact with the volatile organic compound.

2. The gas sensor assembly according to claim 1, wherein the metal oxide nanostructure layer includes zinc oxide nanostructures.

3. The gas sensor assembly according to claim 1, wherein the conductive coating includes a first electrode pattern having a first plurality of finger electrodes and a second electrode pattern having a second plurality of finger electrodes.

4. The gas sensor assembly according to claim 3, wherein the first plurality of finger electrodes and the second plurality of finger electrodes define a channel having a tortuous pattern.

5. The gas sensor assembly according to claim 1, further comprising an ohm meter coupled to the gas sensor, the ohm meter configured to measure the resistance of the metal oxide nanostructure layer.

6. The gas sensor assembly according to claim 5, further comprising a computing device coupled to the ohm meter, the computing device configured to determine the amount of the volatile organic compound.

7. The gas sensor assembly according to claim 6, wherein the inlet assembly includes an intake flow control device.

8. The gas sensor assembly according to claim 7, wherein the computing device is further configured to activate the intake flow control device to pump the gaseous composition into the housing until a pressure setpoint is reached.

9. The gas sensor assembly according to claim 8, wherein the computing device is further configured to activate the ultraviolet light source and determine the amount of the volatile organic compound after the pressure setpoint is reached.

10. The gas sensor assembly according to claim 9, wherein the computing device is further configured to actuate the outlet assembly to remove the gaseous composition out of the housing after determining the amount of the volatile organic compound.

11. An exhaust system comprising:
an upstream conduit configured to carry a gaseous composition having a volatile organic compound;
a scrubber coupled to the upstream conduit and configured to remove at least a portion of the volatile organic compound;
a downstream conduit coupled to the scrubber and configured to carry the gaseous composition from the scrubber;
a first gas sensor assembly coupled to the upstream conduit and configured to measure a first concentration of the volatile organic compound upstream of the scrubber;
a second gas sensor assembly coupled to the downstream conduit and configured to measure a second concentration of the volatile organic compound downstream of the scrubber, wherein each of the first gas sensor assembly and the second gas sensor assembly includes:
a housing;
an inlet assembly configured to carry a gaseous composition having a volatile organic compound into the housing;
an outlet assembly configured to carry the gaseous composition from the housing;
an ultraviolet light source disposed within the housing; and
a gas sensor disposed within the housing and configured to sense an amount of the volatile organic compound; and
a computing device coupled to the first gas sensor assembly and the second gas sensor assembly, the computing device configured to calculate a difference between the first concentration and the second concentration to determine efficiency of the scrubber.

12. The exhaust system according to claim 11, wherein the gas sensor includes:
a substrate;
a conductive coating disposed on a surface of the substrate having a channel defined therein; and
a metal oxide nanostructure layer disposed within the channel, the metal oxide nanostructure layer having a resistance, which varies in response to contact with the volatile organic compound.

13. The exhaust system according to claim 12, wherein the metal oxide nanostructure layer includes zinc oxide nanostructures.

14. The exhaust system according to claim 12, wherein each of the first gas sensor assembly and the second gas sensor assembly further includes:
an ohm meter coupled to the gas sensor, the ohm meter configured to measure the resistance of the metal oxide nanostructure layer.

15. The exhaust system according to claim 14, wherein the computing device is coupled to the ohm meter, the computing device configured to determine the amount of the volatile organic compound.

16. The exhaust system according to claim 15, wherein the inlet assembly includes an intake flow control device and the outlet assembly includes an outlet flow control device.

17. The exhaust system according to claim 16, wherein the computing device is further configured to activate the intake flow control device to pump the gaseous composition into the housing until a pressure setpoint is reached.

18. The exhaust system according to claim 17, wherein the computing device is further configured to:
activate the ultraviolet light source and determine the amount of the volatile organic compound after the pressure setpoint is reached; and
activate the outlet flow control device to pump the gaseous composition out of the housing after determining the amount of the volatile organic compound.

* * * * *